US00PP11988P2

(12) United States Plant Patent
Kuwabara

(10) Patent No.: US PP11,988 P2
(45) Date of Patent: Jul. 10, 2001

(54) HIBISCUS PLANT NAMED 'AUDREY MARI'

(76) Inventor: Hiroshi Kuwabara, 12081 Wagner St., Culver City, CA (US) 90230-5856

( * ) Notice: Subject to any disclaimer, the term of this patent is extended or adjusted under 35 U.S.C. 154(b) by 0 days.

(21) Appl. No.: 09/339,636

(22) Filed: Jun. 24, 1999

(51) Int. Cl.[7] ..... A01H 5/00
(52) U.S. Cl. ..... Plt./257
(58) Field of Search ..... Plt./257

*Primary Examiner*—Bruce R. Campell
*Assistant Examiner*—Anne Marie Grünberg

(74) *Attorney, Agent, or Firm*—Christie, Parker & Hale, LLP

(57) ABSTRACT

A Hibiscus plant particularly producing flowers about 18–20 centimeters (7–8 inches) in diameter. Its heavy texture petals are cartwheel overlapped, and tufted with an undulated petal margin. Its single flower form has a picotee yellow orange (between 19A–21D) edge, red (between 40A–43A) outer body which blends into a slightly redder (near 44A–45A) inner body to a darker red (near 45A–46A) color eye. The plant has medium sized leaves (about 12–14 cm in length and about 11–13 cm in width), cordate to deltoid leaves with somewhat acuminate apices and round smooth bases. Its leaf density is medium to heavy. The plant has an upright medium growth habit and a flower life of three or more days on the plant. Rooting can easily be done via cuttings and the plant is hardy to about 30° F. (0° C.).

5 Drawing Sheets

BACKGROUND OF THE INVENTION

The present invention comprises a new and distinct cultivar of Hibiscus which was originated by crossing the variety known as 'Morning Glory' as *Hibiscus rosa-simensis* seed parent and the variety known as *Hibiscus rosa-simensis* 'Vulcan' as pollen parent. The varietal denomination of this new variety is 'Audrey Mari'. It is not known whether the parent varieties have been patented.

SUMMARY OF THE INVENTION

Among the novel characteristics possessed by the new variety which distinguish it from its parents and all other varieties of which I am aware are its large flowers of attractive coloration and an upright and vigorous plant growth habit.

The following traits have been repeatedly observed and are determined to be basic characteristics of 'Audrey Mari'. Combined characteristics that distinguish 'Audrey Mari' as a new and distinct cultivar include:

1. Cartwheel, overlapped single flower form, and ruffled petal margin.

2. Red (between 40A–43A) petals and picotee yellow orange (between 19A–21D) edge. Red petal outer body blends into a slightly redder (44A–45A) petal inner body to a darker red (45A–46A) color eye.

3. Vigorous, upright, medium growth habit.

4. Continuously blooms during warm weather May (63° F./81° F.) through October (62° F./81° F.) in Southern California.

5. Leaf shape is somewhat cordate to deltoid, acuminate apices with round, smooth base. Leaf margin is moderately serrate. Leaf density is medium to heavy.

6. Flower life is approximately three or more days on plant.

8. Roots easily by cuttings.

Asexual reproduction of the new variety by grafting, as performed in Culver City, Calif., shows that the foregoing and other distinguishing characteristics come true to form and are established and transmitted through succeeding propagations. 'Audrey Mari' may be reproduced by grafting and by vegetative cuttings.

COMPARISON WITH PARENTS

In the photographic illustrations:

*Hibiscus rosa-sinensis* 'Audrey Mari': Started from a seed in 1994. Present year 2000, the instant cultivar displays a faster growth and possesses thicker branches than its parents. 'Audrey Mari' has grown from a one-gallon container to a full size five-gallon container in four (4) years.

*Height.*—122 cm.
*Width.*—70 cm.
*Caliper dimensions.*—30 cm. from the bottom. The average caliper of the branch is approximately 7.5 to 9 mm. The largest caliper dimension of a branch was observed at about 2.0 cm.

*Hibiscus rosa-sinensis* 'Morning Glory': Purchased in 1994 already in a five-gallon container. The specimen was about 30 cm. in height and about 26 cm. wide. The female parent, even after five (5) years, displays slow growth with a pencil size calipers on the lower half of its branches.

*Height.*—55 cm.
*Width.*—58 cm.
*Caliper dimensions.*—30 cm. from the bottom. The average caliper of the branch is approximately 6 to 7 mm. The largest caliper dimension of a branch was observed at about 1.7 cm.

*Hibiscus rosa-sinensis* 'Vulcan': Purchased from a nursery in 1994 already in a five-gallon container. The specimen was about 30 cm. in height and about 29 cm. wide. The male parent, even after five (5) years, displays a slow upright growth rate and is not very bushy.

*Height.*—69 cm.
*Width.*—62 cm.

*Caliper dimensions.*—30 cm. from the bottom. The average caliper of the branch is approximately 5.5 to 6.5 mm. The largest caliper dimension of a branch was observed at about 1.5 cm.

BRIEF DESCRIPTION OF ILLUSTRATIONS

The accompanying illustrations are as follows:

FIG. 1 is a close-up view showing the new variety at the top of the illustration, the seed parent 'Morning Glory' in the lower left and pollen parent 'Vulcan' at the lower right;

FIG. 2 is a close-up view of the reverse surface of a flower of the new variety; and FIG. 3 is a photographic illustration showing the front (top) of an immature leaf on the left side of the photograph and the front (top) of a mature leaf on the right side of the photograph; and FIG. 4 is a photographic illustration of the back (underside) of an immature leaf shown on the left side of the photograph and of the back (underside) of a mature leaf on the right side of the photograph; and FIG. 5 is a photographic illustration showing, on the left, a plant of the variety 'Vulcan' in a five (5) gallon container, in the middle, a plant of variety 'Audrey Mari' in a five (5) gallon container, and on the right, a plant of the variety 'Morning Glory' in five (5) gallon container.

DESCRIPTION OF THE NEW VARIETY

The following is a detailed description of the new variety, from specimens grown in Culver City, Calif., in the month of April. The color terminology used is in accordance with The Royal Horticultural Society Colour Chart (R.H.S.C.C.), and refers to plate numbers in the aforementioned color chart. Phenotypic expression may vary depending on light, environmental and cultural conditions.

Type: *Hibiscus rosa-sinensis.*

Plant:

*Form.*—Mound shape.

*Habit.*—Upright.

*Growth.*—Medium growth habit, height about 122 cm to 244 cm, width about 90 cm to 122 cm; upright growth with medium to thick caliper.

*Foliage.*—Arrangement: Alternate. Size: About 12–14 cm in length and about 11–13 cm in width. Margins: Moderately serrated. Color: Upper side near 137A to 138A; underside near 144A to 146B. Veins: Several minor veins connected to three main veins at base. Petiole: About 6–7 cm. Character: Upper side is moderately grooved with few hairs on groove. Stipules: About 1.5 to 2.5 cm in length with very narrow width (needle shaped); 45° recurve toward the stem and 2 per node; near 143A to 143C. Stem: Aspect smooth, becoming woody with age; major stem near 177B to 177C; branch near 176A to 177A; new shoots near 178A to 178B. Number of sepals: About 5 pointed lobes, single prominent midvein per lobe; membranous.

Bud (1 day prior to opening):

*Size.*—About 8 cm.

*Shape.*—Cylindrical, somewhat like an elongate rosebud.

*Color.*—Near 11A to 13A.

Flower:

*Blooming habit.*—Single flower with very consistent flower color; excellent bloomer during growing season, usually April through November in Culver City, Calif.

*Corolla (petals).*—About 18–20 cm; rounded, tufted with slight undulated margin. Color Upper surface: Near 19A to 21D, picotee edge red between 40A to 43A which becomes slightly redder near 44A to 45A then becomes darker red near 45A to 46A color eye. Underside: Underside of petal overlaps with main vein in center of petal which divides the left side and right side about equally; color of left side of petal, which is exposed, is near 10A to 12A; color of petal of right side, which is overlapped, is near 30D to 32C.

*Pyllaries.*—About 8–9, pointed, narrow, sword-shaped; about 2 cm long; near 146B, located below sepals. Texture: Smooth, slightly shiny and velvety. Shape: Rounded, tufted with slight undulate margin. Substance of phyllaries: Upper surfaces slightly shiny and velvety; undersurface slightly shiny; edge moderately wavy. Size: Phyllaries about 8–10 cm.

*Flower size of character.*—About 18 to 20 cm diameter, cartwheel, overlapped single and ruffled petal margin.

*Peduncle.*—About 2–3 cm, strong, smooth, near 144A.

Reproductive organs:

*Calyx.*—Shape: Sepals joined in a cup (cup shaped). Color: Near 144A to 146B. Length: About 3 to 4 cm.

*Filaments.*—Between red purple to orange white, near 62C to 159D; about 5 mm long.

*Stamens.*—Anthers: About 88. Color: Near 155D. Pollen: Abundant, near 15A.

*Stigma.*—Color: Near 42A to 43A. Number: About 5, rounded, discoid, hairy, about 3 mm diameter.

*Style.*—Length about 6–7 cm long; top about 60% near 159A to 159B; lower about 40% near 45B to 45D.

*Staminal column.*—Length: About 5–6 cm. Base of pistil: Near 45B to 45D.

*Ovary.*—Rounded, near 150B to 151C.

General characteristics:

*Blooming periods.*—Spring, summer and fall (Southern California).

*Hardiness.*—Withstood 30° F. temperature on Dec. 25, 1998 in Culver City, Calif.

*Rooting.*—Good via cuttings.

The leaves shown in FIGS. 3 and 4, were picked on Oct. 3, 2000, and the picture was taken at 3:30 p.m. in the shade.

Mature leaf color:

*Top.*—Somewhere between 137A and 138A.

*Underside.*—Somewhere between 144A and 146B.

*Petiole.*—Somewhere between 187A and 187B.

Immature leaf color:

*Top.*—Near 146B.

*Underside.*—Somewhere between 146B and 146C.

*Petiole.*—Somewhere between 187A and 187B.

I used Green Light® Super Bloom® Fertilizer (12-55-6 with 0.10% Chelated Iron) every two weeks from March to October. I would think fertilizer makes a great difference in coloration of the leaf because nitrogen makes the leaf a darker green color.

In FIGS. 1 and 2, *Hibiscus rosa-sinensis* 'Audrey Mari' — photographic illustration was taken approximately an hour after blooming.

*Hibiscus rosa-sinensis* 'Morning Glory' — picture was taken after second day of bloom.

*Hibiscus rosa-sinensis* 'Vulcan' — picture was taken after first day of bloom.

All photographs were taken around 9:00 a.m. on Apr. 26, 1997, in the morning sun.

*Hibiscus rosa-sinensis* 'Audrey Mari' — measurements were made from a five (5) year old plant. It is grown outside in the morning shade and afternoon sun (no greenhouse or plastic house is used) in Culver City, Calif. The location of Culver City is three (3) miles inland from Marina del Rey Beach (Pacific Ocean).

The average temperatures (degrees in Fahrenheit) in the Culver City area during the year 1997 were:

January: Between 51° F. and 65° F.
February: Between 51° F. and 70° F.
March: Between 54° F. and 74° F.
April: Between 55° F. and 74° F.
May: Between 63° F. and 81° F.
June: Between 64° F. and 78° F.
July: Between 65° F. and 82° F.
August: Between 67° F. and 86° F.
September: Between 69° F. and 89° F.
October: Between 62° F. and 81° F.
November: Between 56° F. and 73° F.
December: Between 49° F. and 67° F.

Rooting: Half hardwood cuttings with misting system. It took about twelve (12) weeks with GRO QUICK electric soil heating cable, built-in thermostat which automatically activates cable when soil temperature is below 74° F., by Wrap-On Co., Inc. 550 West 70$^{th}$ Place, Chicago, Ill 60638. The item costs less than $10.00 which is typically made for home use, with bottom heater, definitely not for commercial use.

*Hibiscus rosa-sinensis* 'Audrey Mari' Five cuttings of half hardwood approximately 15 cm. long each.

Rooting takes place between January and March. The container is kept in a shady area. Rooting Hormone with Fungicide (Rootone) was used on the cuttings before placing in the horticultural sand.

Soil—horticultural sand (by UNI-GRO®) .

Frequency of watering — Misting system three (3) times per day for 15 seconds.

Rate of success 80%.

Place — Culver City, Calif.

The home rooting system used was constructed as follows:

Plastic box approximately 38 cm. square — approximately 35 cm. deep.

GRO QUICK electric soil heating cable was woven into a plastic mesh and placed approximately 2.5 cm. from the bottom.

Approximately 12.5 cm. of horticultural sand was placed in the box.

Misting Drip system (Raindrip®) was placed in a box and attached to a garden hose valve.

Five cuttings each about 15 cm. long were dipped in rooting hormone and placed approximately 5 cm. deep into the sand.

Five air holes were drilled approximately 2.5 cm. from the top around each side of the box (total of 20 holes).

The box was covered with clear plastic which remained on at all times and the box was placed in a shaded area.

Watering was performed three (3) times per day for about 15 seconds with a misting system.

Drainage was at the bottom of the box.

Rate of success was 80%.

Weeks of rooting: Twelve (12) weeks (Softer tip cuttings rooted sooner, harder bottom cuttings took a little longer, but overall the rooting tool approximately 12 weeks).

Place of rooting — Culver City, Calif.

*Hibiscus rosa-sinensis* 'Audrey Mari' is a single flower with five (5) petals.

Fertility: As a Female: 8 seeds (tried once). As a Male 8 to 17 seeds (tried twice).

Fruit: One fruit.

Fragrance: None.

No noted disease or pest resistance. Although this year (2000) in Southern California, according to LOS ANGELES TIMES, Possible Culprits in the Case of Missing Gardenia Blossoms, dated Oct. 5, 2000 there is a giant white fly infestation. I had some giant white fly problems from July to October.

I claim:

1. An Hibiscus plant named 'Audrey Mari' as illustrated and described particularly characterized by its large flower size and its exotic, vibrant coloration.

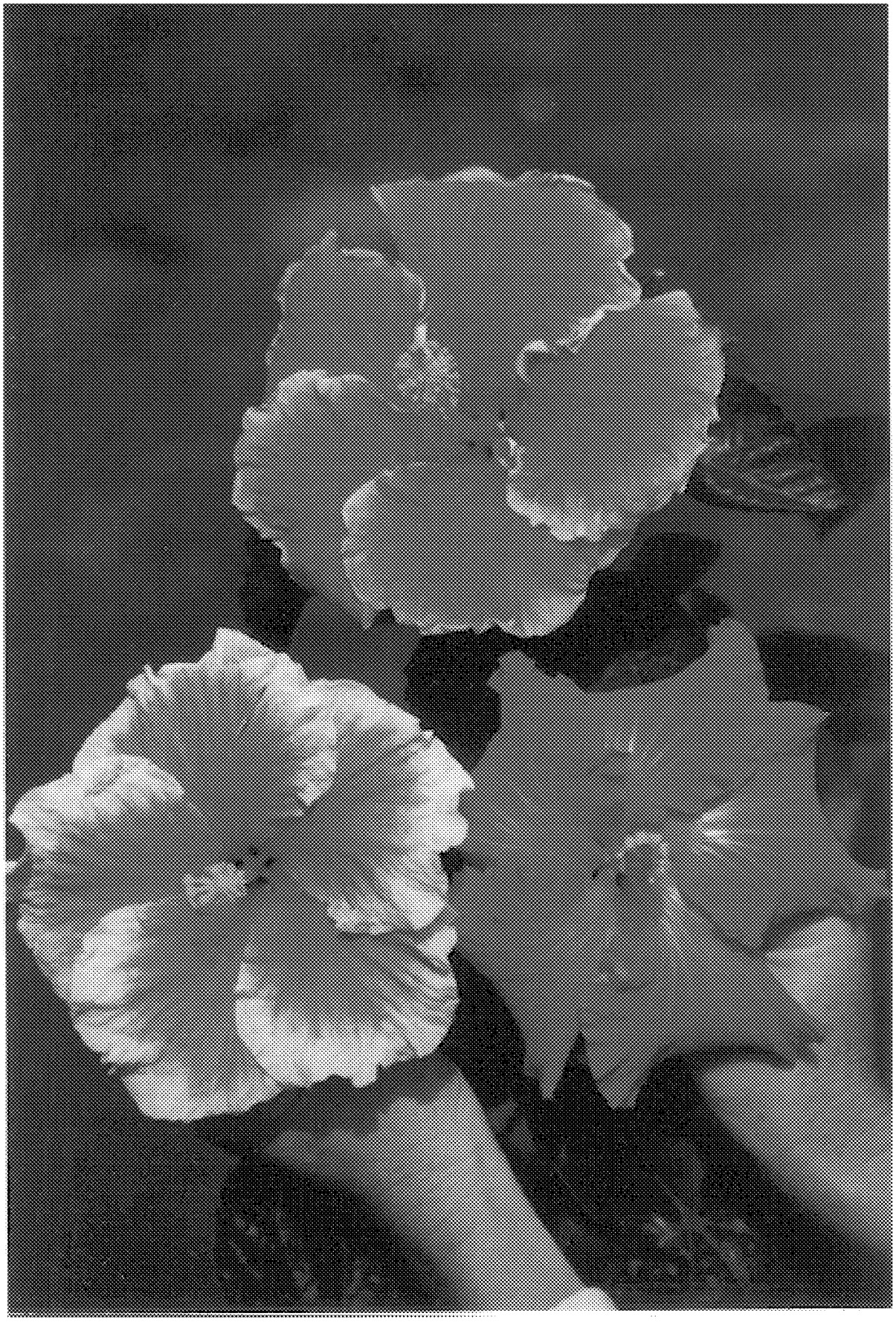

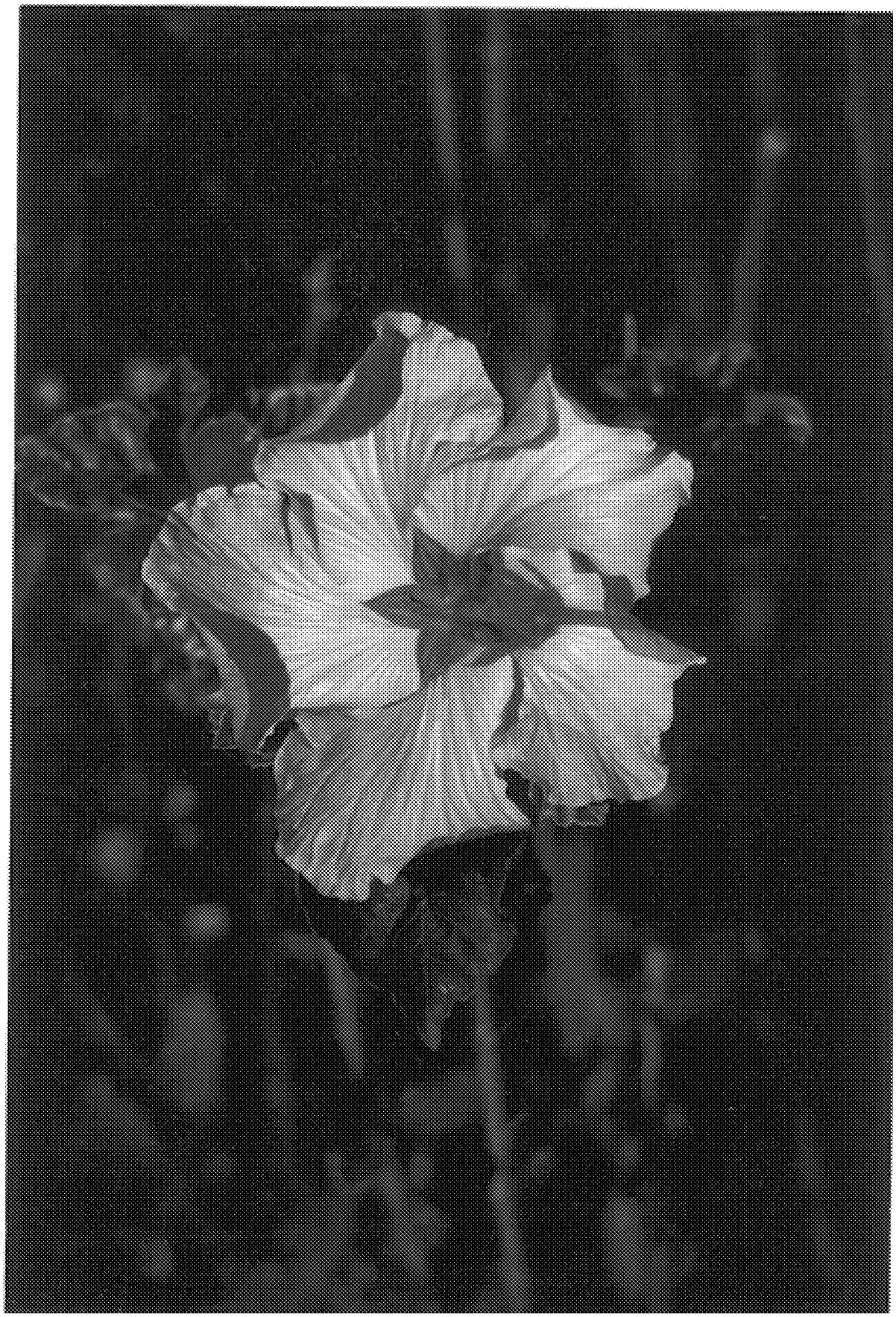

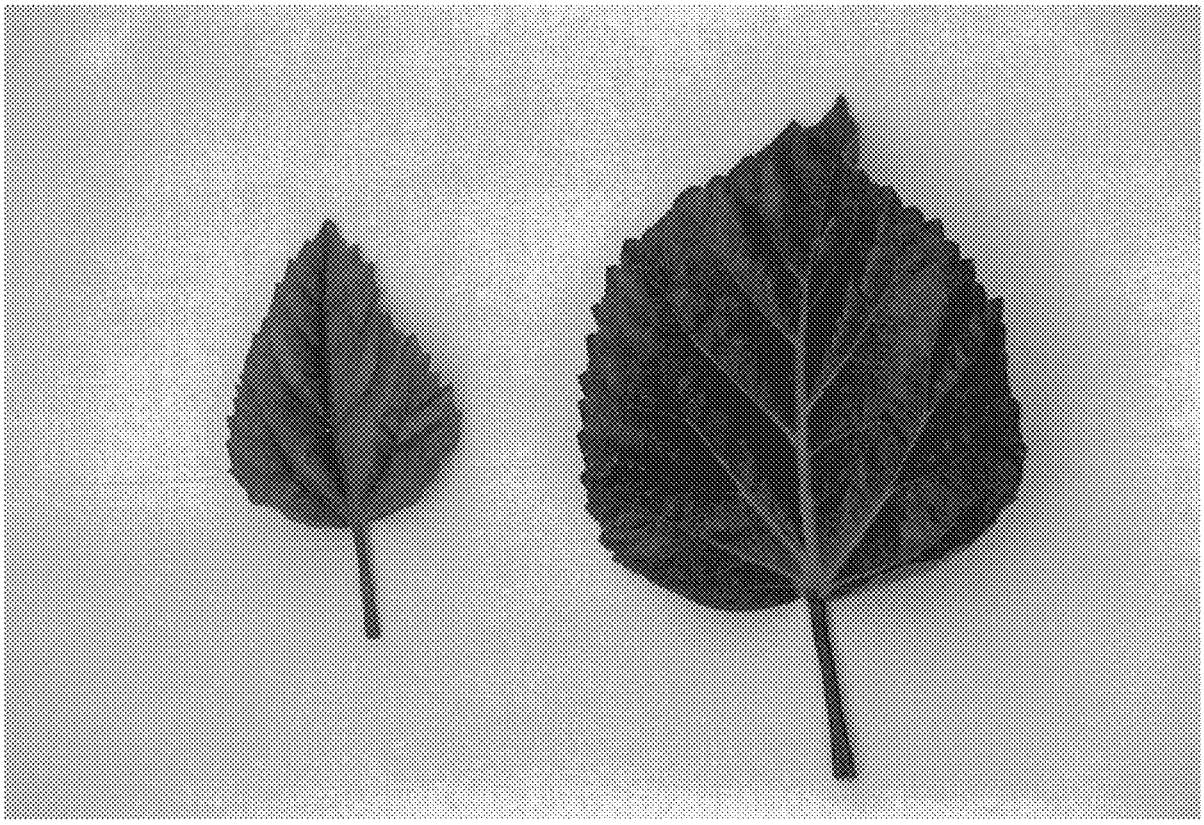

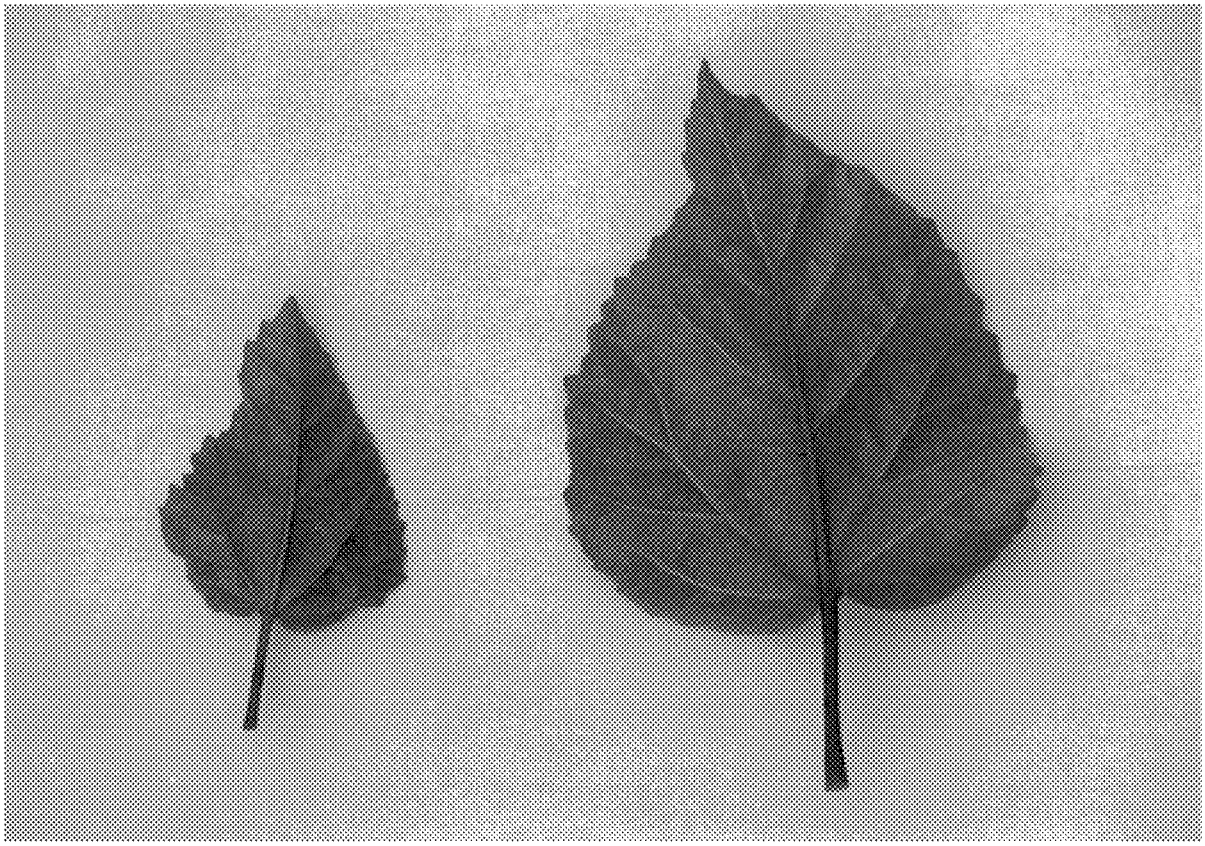

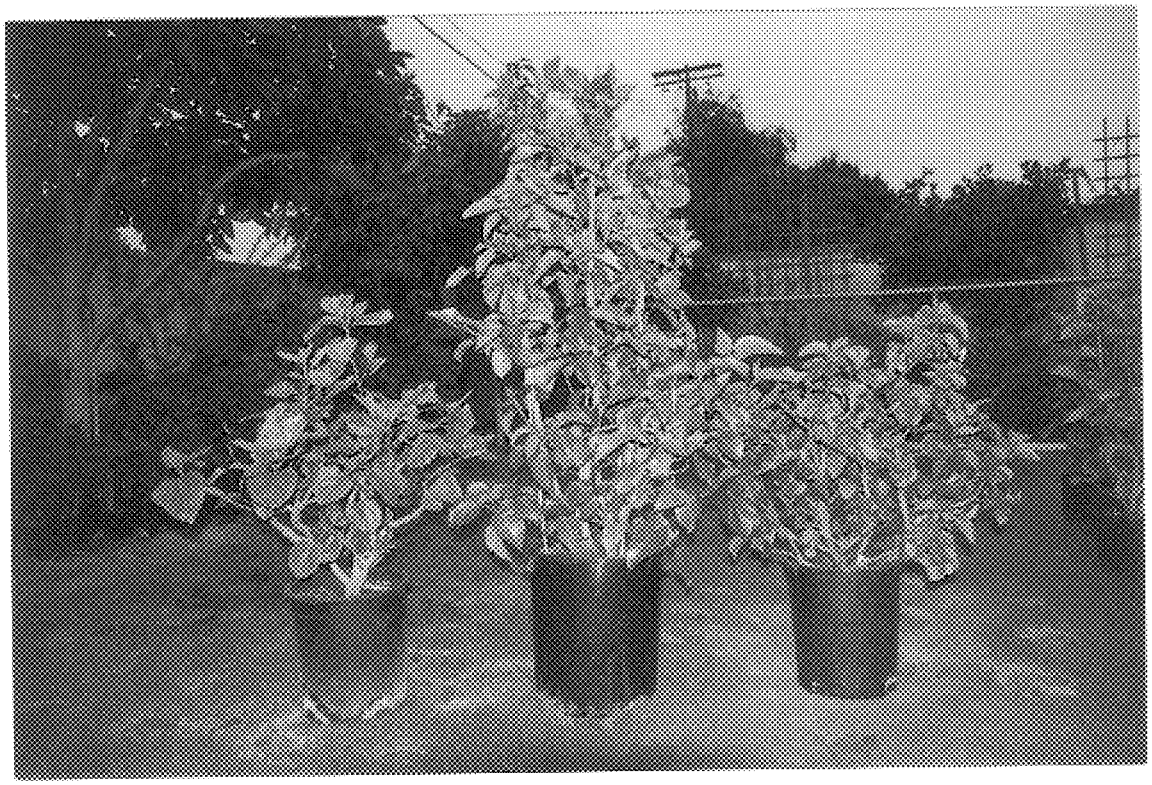

* * * * *